United States Patent [19]

Schmidt et al.

[11] 3,969,347

[45] July 13, 1976

[54] PROCESS FOR THE MANUFACTURE OF THE POTASSIUM SALT OF 6-METHYL-3,4-DIHYDRO-1,2,3-OXATHIAZIN-4-ONE-2,2-DIOXIDE

[75] Inventors: Erwin Schmidt, Kelkheim, Taunus; Karl Clauss, Rossert, Taunus; Hartmut Pietsch, Hofheim, Taunus; Harald Jensen, Frankfurt am Main, all of Germany

[73] Assignee: Hoechst Aktiengesellschaft, Frankfurt am Main, Germany

[22] Filed: July 16, 1975

[21] Appl. No.: 596,217

[30] Foreign Application Priority Data

July 18, 1974 Germany.............................. 2434548

[52] U.S. Cl............................................... 260/243 R
[51] Int. Cl.².......................................... C07D 291/06
[58] Field of Search ................................ 260/243 R

[56] References Cited

UNITED STATES PATENTS 3,917,589   11/1975   Clauss et al......................... 260/243

*Primary Examiner*—John M. Ford
*Attorney, Agent, or Firm*—Curtis, Morris & Safford

[57] ABSTRACT

The potassium salt practically free of fluoride of 6-methyl-3,4-dihydro-1,2,3-oxathiazin-4-one-2,2-dioxide is prepared by cyclization of acetoacetamide-N-sulfofluoride with at least two moles potassium hydroxide, potassium methylate or a mixture of potassium hydroxide and potassium methylate per mole of sulfofluoride in methanol as solvent containing less than 50 % by weight of water at a temperature of from −20° to +60°C and separating the crystalline potassium salt of the oxathiazinone dioxide from the reaction solution. The compound obtained has a pure sweet taste.

5 Claims, No Drawings

PROCESS FOR THE MANUFACTURE OF THE POTASSIUM SALT OF 6-METHYL-3,4-DIHYDRO-1,2,3-OXATHIAZIN-4-ONE-2,2-DIOXIDE

6-Methyl-3,4-dihydro-1,2,3-oxathiazin-4-one-2,2-dioxide as well as the sodium, potassium and calcium salts thereof represent a valuable sweetening agent and especially the potassium salt is distinguished by a pure sweetness.

U.S. Pat. No. 3,689,486 relates to 6-methyl-3,4dihydro-1,2,3-oxathiazin-4-one-2,2-dioxide and the non-toxic salts thereof.

According to this specification acetoacetamide-N-sulfofluoride (I) is subjected to cyclization under the action of bases. With aqueous alkali metal hydroxide solution cyclization proceeds according to the following equation

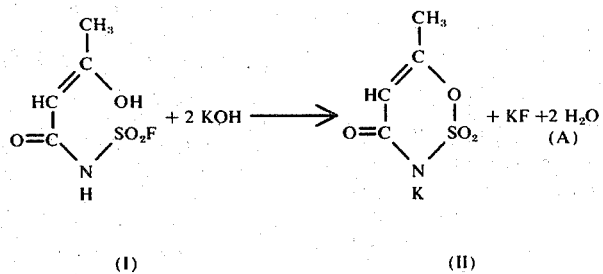

Besides the potassium salt of the oxathiazinone an equimolecular amount of potassium fluoride is formed in a calculated amount of 22.5 % by weight. To isolate the sweetener special processes are necessary, for example acidification of the aqueous solution and selective extraction of the free 6-methyl-3,4-dihydro-1,2,3-oxa-thiazin-4-one-2,2-dioxide with ethyl acetate. The residue remaining behind after concentration by evaporation of the extract can be transformed into the potassium salt by treatment with potassium hydroxide solution.

Hitherto, this method or a similar method had to be used to free the sweetener to a sufficient extent from the toxic potassium fluoride.

It is the object of the present invention to provide a process for the manufacture of the potassium salt practically free of fluoride of 6-methyl-3,4-dihydro-1,2,3-oxathiazin-4-one-2,2-dioxide (II), which comprises reacting acetoacetamide-N-sulfofluoride (I) with at least 2 moles of potassium hydroxide and/or potassium methylate per mole of sulfofluoride (I) in methanol as solvent containing less than 50 % by weight and preferably less than 20 % by weight of water, at a temperature in the range of from −20° to +60°C, preferably 0° to +50°C, and separating the crystalline potassium salt of the oxathiazinone dioxide formed from the reaction solution.

In view of the high solubility of potassium fluoride and the potassium salt of the oxathiazinone dioxide in water, it is very surprising that with methanol the two salts can be separated almost completely in such as manner that the oxathiazinone salt precipitates practically quantitatively while the potassium fluoride remains in solution in contradistinction to the statements in "Landolt-Bornstein" "Zahlenwerte und Funktionen", (6th edition, volume II/2b, Table 3, page 578). The potassium salt of the oxathiazinone dioxide obtained is practically free from fluorides (less than 1 % fluorine) and can be isolated, for example by simple filtration.

The stoichiometric amount of water set free with the use of methanolic potassium hydroxide solution in the cyclization does not have a decisive influence on the separating effect. The sweetening agent of the present invention is obtained practically free of fluoride irrespective of whether solutions of potassium methylate in dried methanol, are used in which case no water is formed, or whether the methanolic potassium hydroxide solution additionally contains water.

For economical reasons it is particularly advantageous to use solutions of commercial potassium hydroxide in technical grade methanol.

To carry out the process of the invention methanol and potassium hydroxide or methylate are mixed at the reaction temperature with the acetoacetamide-N-sulfofluoride, optionally dissolved in an inert solvent, for example methylene chloride, acetone and preferably methanol, and the reaction mixture is stirred until the reaction is terminated.

The reactants can be introduced into the reaction vessel either simultaneously or successively at any order of succession, either continuously or discontinuously.

In order to ensure a satisfactory separation of the salts about 150 to 2,000 ml, preferably 300 to 1,100 ml and still more preferably 500 to 1,000 ml of solvent are used per mole of acetoacetamide-N-sulfofluoride (I).

Potassium hydroxide or methylate should be used in an at least stoichiometric amount according to the aforesaid reaction equation, i.e. at least 2 moles per mole acetoacetamide-N-sulfofluoride (I) or in a slight excess of up to 10 %, preferably up to 5 %, in order to obtain as complete as possible a reaction.

With increasing water content in the methanol the solubility of the potassium salt of the oxathiazinone (II) increases and, therefore, with consideration of the water possibly formed in the reaction, the proportion of water in the reaction mixture should not exceed 50 % by weight, preferably 20 % by weight, calculated on the methanol used.

The concentration of the methanolic alkali metal salt solution can be varied within wide limits and depends on the technical requirements in each case. If the concentration of the methanolic potassium hydroxide solution is above 7 gram equivalents of solute per liter it must be kept fluid by heating and the crystal magma of the sweetening agent must be diluted as otherwise it is difficult to stir. On the other hand, with methanolic alkali metal salt solutions containing less than 0.5 gram equivalent of solute an increasing portion of the sweetener remains in solution. Hence, it proved advantageous to use 1 to 6N methanolic alkali metal salt solutions.

The following examples illustrate the invention.

EXAMPLE 1

183 g acetoacetamide-N-sulfofluoride were introduced, while stirring and cooling to 10° - 20°C, over a period of 30 minutes into 1,200 ml 2N methanolic sodium hydroxide solution prepared from methanol and KOH of about 85 % strength. Stirring was continued for a further 30 minutes, the reaction mixture was filtered with suction, the filter residue washed with methanol and dried at 50°C under reduced pressure. 170 g (85 % of theory) of the potassium salt of 6-methyl-3,4-dihydro-1,2,3-oxathiazin-4-one-2,2-dioxide containing 0.25 % ionic fluorine were obtained.

EXAMPLE 2

A solution of 183 g of acetoacetamide-N-sulfofluoride in 400 ml methanol and simultaneously 600 ml 4N methanolic potassium hydroxide solution, prepared as described in Example 1, were run into a reaction vessel the internal temperature of which was kept at 20° - 30°C. 15 minutes after the addition, the reaction mixture was filtered off with suction, the filter residue washed with methanol containing 5 % water and dried. 172 g (86 % of theory) of the potassium salt of 6-methyl-3,4-dihydro-1,2,3-oxathiazin-4-one-2,2-dioxide containing 0.28 % ionic fluorine were obtained.

EXAMPLE 3

1,000 ml of a solution of 134 g chemically pure potassium hydroxide in 1,000 ml methanol containing 100 g water were dropped, while stirring and cooling to 10° - 20°C, over a period of 30 minutes into a solution of 183 g acetoacetamide-N-sulfofluoride in 300 ml acetone. Stirring was continued for 30 minutes at 30° - 40°C, the reaction mixture was filtered with suction and the filter residue carefully washed with a total amount of about 300 ml methanol and dried under reduced pressure at 50°C. 166 g (83 % of theory) of sweetener (II) were obtained having a content of ionic fluorine of 0.25 % by weight.

EXAMPLE 4

A solution of 183 g acetoacetamide-N-sulfofluoride in 300 ml methylene chloride was added at room temperature, while cooling and stirring, to 1,600 ml 2N methanolic potassium hydroxide solution containing 80 ml water. After suction filtration and washing with methanol, 170 g (85 % of theory) of the potassium salt (II) having a content of 0.4 % by weight ionic fluorine were obtained.

EXAMPLE 5

With the exclusion of humidity 9.3 g metallic potassium were dissolved in 150 ml technical grade methanol (water content 0.12 %) and at 20° - 30°C a solution of 18.3 g acetoacetamide-N-sulfofluoride in 50 ml methanol was added dropwise while stirring. Stirring was continued for 30 minutes at 40°C, the reaction mixture was filtered with suction with the exclusion of humidity and the filter residue was carefully washed with 40 ml methanol. After drying, 15 g (75 % of theory) of the potassium salt (II) containing 0.02 % by weight of ionic fluorine were obtained.

EXAMPLE 6

9.3 g metallic potassium were dissolved in 150 ml technical grade methanol (water content 0.12 %). After addition of 1.80 ml water, a solution of 18.3 g acetoacetamide-N-sulfofluoride in 50 ml methanol was added dropwise over a period of 30 minutes while stirring at 30° - 40°C. After suction filtration, washing with about 40 ml methanol and drying, 15 g (74 % of theory) of the potassium salt (II) containing 0.05 % of ionic fluorine were obtained.

EXAMPLE 7

175 ml 6N methanolic potassium hydroxide solution, prepared as described in Example 1, were added dropwise while stirring at 20° - 25°C to a mixture of 183 g acetoacetamide-N-sulfofluoride and 125 ml methanol. A further 175 ml of the methanolic potassium hydroxide solution were added to the reaction mixture at 40°C while stirring and stirring was continued for 1 hour. The reaction mixture was cooled to 20°C and filtered off with suction. After intense washing with 400 ml methanol and drying at 80°C under reduced pressure 171 g (86 % of theory) of the potassium salt (II) having a content of 0.05 % by weight of ionic fluorine were obtained.

EXAMPLE 8

With the exclusion of humidity 18.6 g metallic potassium were dissolved in 110 ml methanol distilled over magnesium (water content less than 0.03 %) and at 30°C a solution of 36.6 g acetoacetamide-N-sulfo-fluoride in 30 ml absolute methanol was added dropwise at 30°C. After a further 60 minutes the reaction mixture was filtered with suction with the exclusion of humidity, the filter residue was carefully washed with 100 ml anhydrous methanol and dried at 80°C under reduced pressure. 28 g (70 % of theory) of the potassium salt (II) were obtained having a content of ionic fluorine of 0.6 %.

What is claimed is:

1. A process for the manufacture of the potassium salt, practically free of fluoride, of 6-methyl-3,4-dihydro-1,2,3-oxathiazin-4-one-2,2-dioxide by cyclization of acetoacetamide-N-sulfofluoride, which comprises reacting acetoacetamide-N-sulfofluoride with at least two moles potassium hydroxide, potassium methylate or a mixture of potassium hydroxide and potassium methylate per mole of sulfofluoride in methanol as solvent containing less than 50 % by weight of water at a temperature of from −20° to +60°C and separating the crystalline potassium salt of the oxathiazinone dioxide from the reaction solution.

2. The process of claim 1, wherein the methanol contains less than 20 % by weight of water.

3. The process of claim 1, wherein the reaction is carried out at a temperature of from 0° to +50°C.

4. The process of claim 1, wherein the potassium hydroxide, potassium methylate or the mixture of the two compounds is used in an excess of up to 10 % above the stoichiometrically required amount of 2 moles per mole of sulfofluoride.

5. The process of claim 1, wherein 150 to 2,000 ml solvent are used per mole of sulfofluoride.

* * * * *